US009283283B2

(12) United States Patent
Giammona et al.

(10) Patent No.: US 9,283,283 B2
(45) Date of Patent: Mar. 15, 2016

(54) HYALURONIC ACID BASED HYDROGEL AND USE THEREOF IN SURGERY

(75) Inventors: Gaetano Giammona, Palermo (IT); Giovanna Pitarresi, Palermo (IT); Fabio Palumbo, Trabia (IT); Carlo Luca Romano', Milan (IT); Enzo Meani, Milan (IT); Edgardo Cremascoli, Milan (IT)

(73) Assignees: MERO S.R.L., Milan (IT); NOVAGENIT S.R.L., Mezzolombardo (IT)

( * ) Notice: Subject to any disclaimer, the term of this patent is extended or adjusted under 35 U.S.C. 154(b) by 214 days.

(21) Appl. No.: 13/813,422

(22) PCT Filed: Jul. 29, 2011

(86) PCT No.: PCT/IB2011/053384
§ 371 (c)(1),
(2), (4) Date: Jan. 30, 2013

(87) PCT Pub. No.: WO2012/014180
PCT Pub. Date: Feb. 2, 2012

(65) Prior Publication Data
US 2013/0129800 A1  May 23, 2013

(30) Foreign Application Priority Data
Jul. 30, 2010 (IT) .............................. MI2010A1451

(51) Int. Cl.
| | |
|---|---|
| *A61K 47/36* | (2006.01) |
| *A61L 27/20* | (2006.01) |
| *A61L 27/34* | (2006.01) |
| *A61L 27/52* | (2006.01) |
| *A61L 27/54* | (2006.01) |
| *C08B 37/08* | (2006.01) |
| *C08J 3/075* | (2006.01) |
| *C08L 5/08* | (2006.01) |

(52) U.S. Cl.
CPC ................ *A61K 47/36* (2013.01); *A61L 27/20* (2013.01); *A61L 27/34* (2013.01); *A61L 27/52* (2013.01); *A61L 27/54* (2013.01); *C08B 37/0072* (2013.01); *C08J 3/075* (2013.01); *C08L 5/08* (2013.01); *A61L 2300/258* (2013.01); *A61L 2300/402* (2013.01); *A61L 2300/414* (2013.01); *C08J 2305/08* (2013.01)

(58) Field of Classification Search
USPC ........................................... 435/395; 514/54
See application file for complete search history.

(56) References Cited

FOREIGN PATENT DOCUMENTS

| EP | 1666518 | 6/2006 |
|---|---|---|
| EP | 2213315 | 8/2010 |
| WO | WO 2005032417 | 4/2005 |

OTHER PUBLICATIONS

Palumbo F S et al.: "New Graft Coplymers of Hyaluronic Acid and Polylactic Acid: Synthesis and Characterization," Carbohydrate Polymers, Applied Science, Publishers, Ltd. Barking, GB, vol. 66, No. 3, May 2006.
Pitarresi G: "Synthesis of Novel Graft Copolymers of Hyaluronan, Polyethylene Glycol and Polylactic Acid" Macromolecules an Indian Journal, vol. 3, No. 2, Aug. 1, 2007.
International Search Report, PCT/IB2011/053384, Jul. 29, 2011, Applicant: Novagenit S.R.L.

*Primary Examiner* — Walter Webb
(74) *Attorney, Agent, or Firm* — DLA Piper LLP (US)

(57) ABSTRACT

The present invention relates to hydrogels based on hyaluronic acid based derivatives, that are more resistant than hyaluronic acid alone towards chemical and enzymatic degradation and are endowed with a mix of chemical and mechanical properties such that they are of optimal use in several surgeries, for instance for injection in bone fractures or cavities and for the production of coatings of prostheses in orthopedic surgery, as fillers in cosmetic and maxillo-facial surgery, as anti-adhesion barrier in the prevention of postoperative adhesions in abdominal and abdominal/pelvic surgery, and in general surgery. These hydrogels can be loaded with several different kinds of compounds having pharmacological and biological activity, that are then released from the hydrogel in the site of intervention.

16 Claims, No Drawings

HYALURONIC ACID BASED HYDROGEL AND USE THEREOF IN SURGERY

This application is U.S. national stage entry of International Application No. PCT/IB2011/053384 filed on Jul. 29, 2011, which in turn claims benefit of priority of Italian Patent Application No. MI2010A001451 filed on Jul. 30, 2010, the contents of each of which are hereby incorporated by reference in their entirety.

FIELD OF THE INVENTION

The present invention relates to a hydrogel obtained from derivatives of hyaluronic acid useful as carrier of bioactive compounds, and its use in various fields of surgery such as, e.g., cosmetic surgery, maxillofacial surgery, abdominal surgery, general surgery, and in particular in the orthopedic field; in the orthopedic field, the gel of the invention is useful for the production of coatings of prostheses for implant in the human or animal body. In a preferred embodiment, the invention relates to a hydrogel loaded with bioactive compounds.

STATE OF THE ART

Compositions based on hyaluronic acid or its derivatives, for instance in form of hydrogel, are known for use in various fields of surgery.

Hyaluronic acid is used in cosmetic surgery alone (as biorevitalizing) or derivatized with various molecules (use as filler); this use is described, e.g., in the papers "Hyaluronic acid: biological role and clinical applications", P. Brun et al., J Plastic Dermatol. 2005; 1:21; "Il recupero dell'elasticità e del turgore cutaneo mediante iniezione intradermica di acido ialuronico (IaI-System®) con tecnica cross-linked", A. Di Pietro et al., Giornale It. Dermatol. Venereol. 2001; 136:187; and "Facial wrinkles correction and skin rejuvenation (biostimulation) by auto-cross-linked hyaluronic acid", A. Di Pietro et al., Journal of Plastic Dermatology Vol. 3, n°2 May-August 2007. Commercial products based on hyaluronic acid-based systems are, for instance, those known as IaI System® or IaI System Acp® (registered marks of Fidia Farmaceutici S.p.A.), Restylane® and Perlane® (registered marks of HA North American Sales AB), and similar.

The use of hyaluronic acid or its derivatives, for instance in form of gel or similar products, is more and more frequent also in abdominal surgery; in this case, these products have the object of preventing the formation of post-surgical abdominal adhesions. Adhesions are possible complications that may arise by a term of five days following operations, due to a natural body response to an abdominal or gynecological trauma. These are fibromatosis bands made of scar tissue connecting organs and tissues normally separated from each other. All abdominal/pelvic organs are covered by a thin membrane named peritoneum. Any lesion of this membrane is the starting step for the formation of adhesions. Any lesion is in fact followed by a reparation process. If, however, the injured peritoneal surface is in contact with another surface, a re-epithelialization process takes place that, in a sense, "merges" the two surfaces creating an adhesion. Adhesions formation is thus a normal consequence of operations, due to regenerative processes of the body producing a scar response going beyond the necessary level, creating potentially invalidating clinical conditions.

The appearance of adhesions is by no means infrequent: they develop in about 93% of patients subjected to abdominal or pelvic surgery, such as operations to treat abdominal hernia, gynecological operations, colo-rectal operations and many others.

Adhesions may cause serious complications, among which, small intestine obstruction, women infertility, debilitating chronic pain, and difficulty in carrying out new operations in already treated sites. Post-surgical adhesions cause in fact 74% of intestinal obstructions and are responsible for 20-50% of cases of chronic pelvic pain. Moreover, adhesions are one of the main causes of female infertility, being responsible of 15-20% of cases.

Besides, the presence of adhesions makes it difficult a new intervention in an already surgically treated site. It is indeed necessary to remove the exceeding scar tissue in order to have access to the site to be treated (so called adhesiolysis). Although adhesions are very frequent and common, to date the knowledge of the problem, and in particular of the ways to avoid it, is still poor. The only remedy effective to date for treating adhesion pathologies is surgery, carried out both in laparoscopic and traditional way: there are no known drugs capable to eliminate the adhesion once this is formed; the rate of recurrence after operation is however high, so recourse is had to intervention only in case of real need, for instance obstructive complications or recurrent painful symptomatology.

The use of hyaluronic acid derivatives to prevent these post-surgical complications is described for instance in U.S. Pat. No. 6,723,709 B1 (products based on cross-linked hyaluronic acid), or in the papers "Prevention of postoperative abdominal adhesions by a sodium hyaluronate-based bioresorbable membrane: a prospective, randomized, double-blind multicenter study", J. M. Becker, et. al., J. Am. Coll. Surg., October 1996, 183 (4), pages 297-306, which describes a membrane based on hyaluronic acid and carboxymethylcellulose; and "Prevention of Postsurgical Adhesions with an Autocrosslinked Hyaluronan Derivative Gel", C. Belluco et. al., Journal of Surgical Research, Vol. 100 (2), October 2001, pages 217-221, which describes the use of cross-linked hyaluronic acid. Products based on these systems are marketed for instance by the company Genzyme Biosurgery and by the company Fidia Farmaceutici, which have developed products based on hyaluronic acid (Fidia), in combination with carboxymethylcellulose (Genzyme). The products on the market to this end are based on cross-linked hyaluronic acid alone (Hyalobarrier; Hyaloglide), or in combination with other polysaccharides, such as carboxymethylcellulose (Seprafilm; Sepragel) and in the form of films, such as Surgi-Wrap, a polylactic acid film.

The techniques and the products developed for the cosmetic and abdominal surgery have use also in general surgery, for instance in gynecology.

Finally, another important sector of application of hyaluronic acid and its derivatives in the medical field is orthopedics.

Orthopedics is the branch of surgery dealing with fixation, repairing or reconstruction of damaged bones, also applied in fields such as traumatology, neurosurgery and maxillo-facial surgery.

A technique commonly used in orthopedics is the insertion of implants in the body for the fixation or reconstruction of bones and their parts. Implants are generally made of biocompatible metals (in particular titanium, cobalt-chrome, etc.), polymers, ceramics, hydroxyapatite, or their combinations (e.g., metals coated with a layer of hydroxyapatite). The technique is generally used in osteosynthesis, joint replacements, orthopedic and traumatological bone reconstruction, spine surgery and maxillo-facial and odonthoiatric applications. Implants may be used to replace, at least partially, damaged bones, joints or teeth; or, they may be aid means used to fix bone parts or help these to keep the correct spatial relationship; in this second case the implants may be bone fixation plates (e.g., craniofacial, maxillo-facial, orthopedic, skeletal and the like), nails, screws, scaffolds and the like. The term "prosthesis" would be more appropriate for devices of the first kind, but as used in the present invention, it will be intended to mean both an actual prosthesis and any other aid means to be inserted in the human or animal body for the applications cited above.

Another technique adopted in orthopedics is the injection of biocompatible materials in damaged parts of bones, such as fractures or holes; the latter may result by the removal from bones of temporary implants, such as screws. The biocompatible material in this case fulfills the function of temporarily replace the bone tissues, in order to maintain mechanical resistance, for the period necessary for such tissues to grow and fill the damaged area or space.

The area of the body involved in an orthopedic surgical operation may be subject to post-operation problems; or, even if such problems do not arise and postoperative course is smooth, it may be required the local administration of agents that facilitate recovery from the operation.

A first possible problem in orthopedic surgery is that of bacterial infections. For example, about 4.3% of orthopedic implants realized in the USA give rise to bacterial infections (E. M. Hetrick et al, "Reducing implant-related infections: active release strategies", Chem. Soc. Rev. 2006, 35, 780-789).

Many studies have documented the transfer of organisms from personnel in the operating theater to the patient during surgical interventions; see, e.g., Bather C. J. et al, "The effects of 'in-use' surgical handwashing on the pre- and postoperative fingertip flora during cardiothoracic and orthopedic surgery", Journal of Hospital Infection, (1995) 30, 283-293.

Acute or chronic osteomyelitic infections may also develop in many cases of osteosynthesis after bone fractures. In situations in which an inert foreign body is implanted into an already injured and weakened tissue, a competition develops for the colonization of the implant surfaces between bacteria (such as *Staphylococcus Aureus*, which has often been found in cases of contaminated bone fractures) and the cells of the immune system. However, bacteria have the advantages over immune system cells of faster reproductive processes and an extreme flexibility in adapting to the environment. Moreover, studies indicate that the procedures for implanting a prosthesis, and the presence of the prosthesis itself in the site of bone fracture, damage the local immune system response with the result that the number of bacteria required to cause an infection can fall by a factor of even 10,000 (Flückiger U. et al, "Factors influencing antimicrobial therapy of surface adhering microorganisms", Recent Res. Devel. Antimicrob. Agents Chemother., (2000) 4, 165-175).

A standard implantation technique for prostheses and osteosynthesis consists of extensive removal of the necrotic and damaged tissue, cleaning of the cavity, implanting of a prosthesis and systemic parenteral prophylaxis with antibiotics. Similar procedures are adopted in case of injection of fluid biomaterials in fractures or bone cavities. The systemic release of antibiotics involves certain drawbacks such as systemic toxicity, reduced absorption into the ischemic or necrotic tissues and prolonged hospitalization to monitor drug levels and their effects. In cases in which bacterial colonization of the treated part is not efficiently avoided by systemic prophylaxis, a new surgical intervention (especially in case the replacement of the prosthesis turns out to be necessary) and a long term systemic antibiotic therapy, possibly with an extension of the hospitalization period may be required, resulting in further discomfort for the patient. To avoid that bacterial colonies become established, use may be made of antibacterial agents, most commonly antibiotics but that may also be of other kinds.

Another problem unavoidably connected to orthopedic surgery is postoperative pain. Pain is always felt by patients when the effects of anesthetics fade out, generally a few hours after surgery, and is most intense about 2-3 days after the operation.

To cope with this problem, it is known to have recourse to analgesics, that may belong to various classes, such as non-steroidal anti-inflammatory drugs (NSAIDs), opioid analgesics or local use anesthetics.

Finally, it may be desirable to provide in the site of operation agents that favor recovery from the operation itself and its consequences; these agents are generally referred to as growth factors.

For the sake of brevity, all substances recalled above, having a biological or pharmacological activity and used in post-operative practice, are simply referred to cumulatively as "bioactive compounds" in the present description, unless in cases when these are named individually.

Several researchers have proposed to adopt in orthopedic surgery materials capable of acting as vehicles, directly in the operation site, of bioactive compounds. The functional requirements of these materials are that they should be biocompatible (or bionert), and possibly bioreabsorbable after the period of activity of the bioactive compounds; they should not be easily degraded by bodily fluids; they must of course not be themselves prone to colonization from bacteria, a property indicated in the field as "anti-fouling"; they should preferably be capable of releasing an active principle immediately after the intervention and at least during the following 6 hours, preferably up to 48-72 hours, so as to cover the part of the postoperative period that is most critical at least with respect to the antibacterial action and pain control; and, in the case of implants, these materials should have rheological and adhesion properties over the prostheses such that the material does remain onto the prosthesis, and is not completely removed by the shear stresses induced by insertion in the cavities prepared for the same (in order to exert their best action, a prosthesis must in fact make a tight contact with the surfaces of the seat provided for it in bones).

The needs pointed out above for orthopedics are mostly valid for maxillo-facial surgery as well.

Various carriers for local drug release have been developed and used, such as polymethylmethacrylate (PMMA) beds onto which the drug is loaded. These materials are however not reabsorbed and require subsequent intervention for their removal. Moreover the low porosity of the PMMA bed inhibits drug release by 25-50%, thus reducing the drug quantity released and increasing the risk of selection of bacterial mutants resistant to the active principle.

Biodegradable materials offer the advantages of bioreabsorption, which avoids subsequent intervention to remove them, reduces reactions induced by foreign bodies, and increases total release of the drug locally; besides, the kinetics of drug release from the matrix can be modulated by controlling the matrix degradation processes.

A known biodegradable and bioreabsorbable polymer is hyaluronic acid. Hyaluronic acid (also indicated as HA in the rest of the description) is a generic name for heteroglycane polymers derived from the repetition of a basic unit comprising D-glucuronic acid and N-acetyl-D-glucosamine. HA, in the forms naturally occurring in many animal tissues, may have a molecular weight (MW) ranging from about 5,000 to about 20 millions Dalton (Da), and the properties of a specific sample of the compound may vary depending on its actual MW. HA is a fundamental component of the extracellular matrix (ECM) and is essential for good operation of numerous body tissues such as connective or epithelial tissues, and in the inner ear fluids, in the vitreous humour of the eyes and also in the liquid essential for the joints (synovia). It is a highly biocompatible and biodegradable polymer with well-known anti-adhesive and lubricity properties, the latter exploited in International patent application WO 2004/014303 A2. However, HA as such is not suitable for injection or for the coating of prostheses, due to its rapid degradation by hyaluronidases, enzymes naturally occurring in the human and animal body; as a consequence of such rapid degradation, drug release over the required period cannot be guaranteed. Furthermore, due to its high hydrophilicity, a coating produced with HA would not have sufficient mechanical stability when a prosthesis is implanted in the body, that is, an essentially water-based environment. HA derivatives have been studied in view of various possible medical applications. International patent application WO 2006/069578 A1 discloses copolymers of HA with polymers of alpha hydroxyl acids or other polymers, for different uses in the cosmetic or medical field; this document does not cite the use of these HA-based copolymers for injection in the body or the treatment of prostheses.

Patent EP 1773399 B1 discloses compositions obtained by cross-linking HA with a polyhydrazide; these compositions form hydrogels when contacted with water. International patent application WO 2010/061005 A1 discloses copolymers of HA obtained via a two-step process, in which in the first step at least one hydroxyl group of HA is reacted with a carbonilating agent to obtain an activated intermediate, and in the second step the thus obtained intermediate is reacted with a reactive nucleophile containing at least one primary amino group; the result is a form of HA functionalized with side-chains which are linked to the backbone of the acid through a carbamic group. Patent application US 2004/0013626 A1 discloses nanoparticles to be used as drug vectors, formed of a polymer obtained by grafting at least one molecule of a polysaccharide to a biodegradable polymer different from the polysaccharide, preferably a polyester.

The paper "New amphiphilic lactic acid oligomer-hyaluronan conjugates: synthesis and physicochemical characterization", Pravata L. et al, Biomacromolecules (2008) 9, 340-348, describes a HA derivative produced by grafting lactic acid oligomers (OLA), of average molecular weight around 500 Da, to hydroxyl radicals of the acid. These HA-OLA derivatives show lower hydrophilicity than HA and modified rheological properties compared to the same, making them more stable in an aqueous ambient, while maintaining good biodegradability and bioreabsorption characteristics.

The paper "New graft copolymers of hyaluronic acid and polylactic acid: synthesis and characterization", Palumbo F. S. et al, Carbohydrate Polymers (2006) 66, 379-385, describes HA derivatives obtained by grafting poly-lactic acid (also abbreviated PLA in the rest of the description) to a HA of average MW of 266,000 Da with two different substitution degrees, in the first case a ratio PLA chains to HA repeating units of 1.5%, in the second case a substitution degree of 7.8%; the first compound is still rather hydrophilic, while the second is more hydrophobic and gives rise to gel-like dispersions in water. This paper indicates some possible applications of the disclosed graft copolymers in the biomedical field, such as the use of their aqueous solutions to reduce adhesion after abdominal surgery, in ophthalmic procedures and for the lubrication of joints, but no hint is given to possible uses in orthopedic implants.

The paper "Synthesis of novel graft copolymers of hyaluronan, polyethyleneglycol and polylactic acid", Pitarresi G. et al, Macromolecules an Indian Journal, Vol. 3, Issue 2, August. 2007, 53-56 describes HA derivatives obtained by grafting onto the HA chain both PLA and polyethylene glycol (abbreviated PEG), showing that these latter are less hydrophobic than compounds obtained by HA and PLA alone.

International patent application WO 2005/032417 A2 discloses a coating produced using a physical mixture of HA with one or more biocompatible polymers, among which PLA, and loaded with an antimicrobial agent; this document also discloses the use of said mixture to produce a dry film charged with the antimicrobial agent onto the surface of a prosthesis, for subsequent implant. Prostheses coatings produced according to this document however suffer of at least two drawbacks: first, the antimicrobial agent, e.g. an antibiotic, has a limited lifetime, so it may not be completely efficient at the time of implant; second, this method does not allow to tailor the prosthesis coating to the specific requirements of the different cases, for instance, known intolerances of a patient to a given antibiotic, or the need to adopt a particular antibiotic, or a specific level of dosage of the same, in a specific situation.

Patent application EP 1666518 A1 discloses drug carriers derived from a HA modification product, in which polyester chains (selected from polylactic acid, polyglycolic acid, and lactic acid-glycolic acid copolymers) are grafted onto the base HA chain. As stated in this document, and shown in all the formulas shown therein, the grafting of the polyester to the HA chain occurs by bonding, either directly or through di-amino or di-hidrazide spacers, to the carboxylic groups present on the glucuronic acid moieties of HA. This way, at least part the carboxylic groups of HA are transformed into amide groups; as the free carboxylic groups are responsible of the hydrophilicity of HA, the modification proposed in this document leads to a reduction of said hydrophilicity; in fact, the modified HA chains of EP 1666518 A1 exhibit a tendency to coil on themselves, making these products suitable for the production of micro- or nanospheres used as injectable drug carriers according to an aspect of the invention disclosed in the cited document. Besides, the compositions disclosed in this document are aimed and tailored to the sustained release of the drug, during a period longer than several days (see paragraph [0007] of the document), but this feature is not desirable in the specific field of orthopedics.

Finally, the paper "Self-assembled amphiphilic hyaluronic acid graft copolymers for targeted release of antitumoral drug", Pitarresi G. et al, Journal of Drug Targeting, 2010, Vol. 18, Issue 4, 264-276, describes a modified form of HA obtained by grafting onto the backbone of HA polylactic acid chains, alone or in combination with polyethylenglycol chains, and dissolving the thus obtained graft copolymers in water at a maximum concentration of 2.4 mg/ml (equal to 0.24% w/v) in order to obtain a micellar dispersion of the copolymer able to transport entrapped drug molecules (Doxorubicin exemplified in the paper).

There is thus a need in the field for improved carriers of bioactive compounds for use in orthopedic surgery, not suffering the drawbacks of the prior art; similarly, it is felt the need of having available products still better than those already present in the market for the other cited surgeries, that is, cosmetic, abdominal, maxillo-facial and general surgery.

SUMMARY OF THE INVENTION

It is thus an object of the invention to provide a hydrogel comprising a hyaluronic acid derivative for use both in orthopedics, and in cosmetic, abdominal, maxillo-facial and general surgeries, alone or in combination with a bioactive compound.

It is another object of the invention to provide compositions containing a hydrogel comprising a hyaluronic acid derivative and at least a bioactive compound.

It is a further object of the invention to provide prostheses for implant in the human or animal body coated with the above cited hydrogels based on hyaluronic acid derivatives, possibly containing a bioactive compound.

DETAILED DESCRIPTION OF THE INVENTION

In a first embodiment, the invention provides a hydrogel comprising water and a hyaluronic acid derivative wherein:
the hyaluronic acid derivative comprises hyaluronic acid, or a salt thereof, of molecular weight comprised between 50,000 and 3,500,000 Da onto the N-acetyl-D-glucosamine moieties of which are grafted chains of a biodegradable and biocompatible polyester of molecular weight comprised between 3,000 and 900,000 Da, in an amount such that the derivative comprises between 1 and 50 of said polyester chains per 100 repeating unit D-glucuronic acid/N-acetyl-D-glucosamine of hyaluronic acid; and
the hyaluronic acid derivative concentration is between 1 and 35% w/v.

The inventors have found that, starting from a particular class of HA derivatives, it is possible to produce a hydrogel that is more resistant than HA alone towards chemical and enzymatic degradation and is endowed with a mix of chemical and mechanical properties such that it can be used for injection in bone fractures or cavities and for the production of coatings of prostheses. Though in the following description reference is made to hyaluronic acid, it is understood that by this term are meant as well salts of the acid normally present in a human or animal body, such as salts of $Na^+$, $K^+$, $Mg^{2+}$ or $Ca^{2+}$. In particular, the inventors have found that by grafting the biocompatible polyester onto the N-acetyl-D-glucosamine moieties of HA, through reaction with the free hydroxy group present in these moieties, the HA derivative maintains high hydrophilicity, combined with properties of viscosity and retention of this viscosity with time, as well as fast release of the bioactive compound, that make these derivatives extremely well suited for applications in the orthopedics field. This is contrary to the teaching of the cited document EP 1666518 A1, in which the grafting of polyester side-chains takes place onto the carboxilic acid groups instead, leading to a reduced hydrophilicity.

All percentages in the following description are expressed as weight/volume percent values (w/v %, that indicates the mass of solute, in grams, per 100 ml of the solution or of the resulting gel) unless it is specified otherwise.

The main component of the hydrogel is a hyaluronic acid derivative, obtained by grafting chains of biodegradable and biocompatible polyesters onto a fraction of the acid having molecular weight in a particular range.

The useful fraction of HA, to be used as starting material in the preparation of the derivative, has a molecular weight (MW) comprised between about 50 kDa and 3.5 MDa, preferably between 100 kDa and 1.5 MDa and more preferably of about 200-300 kDa. HA of MW in these ranges may be obtained by degradation of higher fractions of HA in strongly acid environments, as described in the paper "Disulfide crosslinked hyaluronan hydrogel", Shu X. Z. et al, Biomacromolecules (2002) 3, 1304-1311. The starting material may be obtained from natural sources (e.g., rooster combs); in alternative, it may be produced by microorganisms (as described e.g. in patents U.S. Pat. No. 4,801,539 and EP 694616) or from recombinant routes (as described e.g. in patent applications WO 03/054163 and WO 2006/069578). Synthetic pathways (from microorganisms or recombinant route) may also be adapted to produce HA already in the desired MW range, that thus does not need a degradation step.

The other reactant in the production of the derivative is a biodegradable and biocompatible polyester or a mixture of polyesters or copolymers thereof. The most interesting polyesters for the aims of the invention are poly-lactic acid, polyglycolic acid, poly-caprolactone (these latter also referred to in the rest of the description as PGA and PCL, respectively), their mixtures and copolymers. It has been found that hydrogels of desired properties can be prepared with HA derivatives produced with polyesters having a MW in the range between 3-150 kDa in the case of PLA, in the range 1-900 kDa in the case of PGA, and in the range 3-900 kDa in the case of PCL or of copolymers PLA-PGA (also referred to as PLGA hereinafter) or copolymers comprising PCL. These compounds are commercially available, for instance from Boehringer Ingelheim or from resellers of chemicals, such as Fluka or Sigma-Aldrich.

In order to enhance the reactivity of the polyester, it is preferable to activate its carboxylic end by reaction with a good leaving group, e.g. an imide, preferably N-hydroxysuccinimide (NHS), or with an agent such as carbonyldiimidazole (CDI), which converts a carboxylic acid into the corresponding imidazolide, the reactive form of an acylating agent. The formation of these polyester—NHS compounds is carried out through a first reaction of the free carboxyl group of the polyester with dicyclohexylcabodiimide (DCC) and then functionalizing it with NHS; the reaction is carried out, e.g., at room temperature for 24 hours.

Owing to the fact that HA is a strongly hydrophilic compound, while the above polyesters (even when activated with NHS) are hydrophobic, it is necessary to render one of the reactants compatible with the solvents suitable for the other reactant. According to the present invention, this result is obtained by transforming HA into an ammonium salt, such as the cetyltrimethylammonium (CTA) or preferably the tetrabutylammonium (TBA) salt. The formation of the ammonium salt may be simply carried out by neutralizing HA with the hydroxide of the ammonium cation. The reaction proceeds with 100% yield, and the resulting product in soluble in dimethyl sulfoxide (DMSO), in which the polyesters and their —NHS derivatives are soluble as well. In case HA is available in the form of one of its inorganic salts (e.g., the sodium salt, the most common commercial form of HA), it is possible to first pass an aqueous solution of the same through an acid ion-exchange column, or treat it with an acid, in order to recover HA in acid form.

The ammonium-substituted HA and the polyester-NHS compound are then reacted in DMSO in the presence of diethylamine (DEA) as a catalyst; the reaction takes place e.g. in 24 hours at 40° C. The reaction consists in the condensation of the carboxylic function of the polyester (activated with NHS) with the hydroxyl group of the N-acetyl-D-glucosamine units of HA. The ratio of N-acetyl-D-glucosamine units to which is grafted a polyester chain to the total number of such units present in the HA is defined in the present invention "derivatization degree". The inventors have found that hydrogels of desired properties can be produced with HA derivatives in which said derivatization degree is comprised between 1 and 50%.

The properties (in particular the hydrophilicity and antifouling characteristics) of the HA derivative may be further modulated through a second derivatization, in which a part of the carboxyl groups of the D-glucuronic acid of HA are functionalized with polyethylene glycol (PEG) chains. PEG is known to be a biocompatible polymer (it is approved by the FDA) and is widely used in the pharmaceutical field both for preparing conventional dosage forms and for innovative release systems. Best final results are obtained when the PEG employed has a MW between 400 Da and 20 kDa, preferably of about 5 kDa, and the derivatization degree of HA with PEG (namely, the ratio of D-glucuronic acid units derivatized with PEG to the total number of such units in the HA) is comprised between 5 and 20%.

PEG is preferably pre-activated to enhance its reactivity, through exchange of the free-OH group at one end thereof with —$NH_2$ (PEG-$NH_2$); the latter compound is also available commercially. PEG-$NH_2$ is added in DMSO to the reaction product of ammonium-substituted HA and polyester-NHS, after the latter has been isolated by precipitation of the reaction mix with a non-polar solvent (e.g., diethyl ether), filtration and repeated washing with acetone to eliminate any non reacted polyester-NHS. The HA derivatives thus obtained (with or without PEG) are then purified by means known to the skilled in the art, e.g., dialysis and freeze-drying, and possibly subjected to ion exchange to exchange the ammonium ions with $Na^+$ or $K^+$ ions, more compatible with the intended use.

The HA derivative is then added to water, that normally can be bidistilled water, a buffer saline solution, a sterile physiological solution or water for injectable preparations, in such an amount that its concentration in the resulting hydrogel is comprised between 1 and 35% w/v, preferably between 2 and 10% w/v. Operating as described so far, all concentrations of HA derivative between 1 and 35% w/v give rise to uniform transparent viscous gels. These hydrogels are stable for long periods, and can be stored for at least six months even at ambient temperature without altering their properties, in particular their viscosity.

Due to the very adaptability of the hydrogel that may be obtained both with different derivatization degrees and with different concentrations, always showing anyway the required viscoelastic properties, the use of the same is tunable in view of the type of surgery.

In fact, for use in orthopedics or abdominal surgery the product viscosity must be high in order to ensure the barrier effect against the adhesion of inflammatory and/or bacterial cells in case it is used in orthopedics, or of obstacle against a re-epithelialization process in the case of abdominal surgery. In the case of an operation with laparotomy or laparoscopy techniques, the product in form of hydrogel can be associated to an anti-inflammatory drug, for instance ibuprofen, in order to reduce at a minimum the risk of inflammation during surgical intervention due to fibrous-scar processes.

In case of a septoplasty or rhinoplasty operation (maxillo-facial surgery), interventions are effected directed to reduction and re-shaping of the cartilage and bone skeleton, and the hydrogel of the present invention is used to sustain the nasal structures during reparation; the hydrogel must consequently have high viscosity, as in the case of orthopedics or abdominal surgery; the product in form of hydrogel can be associated to a local anesthetic to reduce to a minimum the pain caused by operation, for instance ropivacain, widely used in nose surgery.

In case, instead, in which the use is addressed to cosmetic surgery, the viscosity of the product is of the utmost importance. In this case, in fact, the hydrogel of the present invention must not be too viscous, as the product has to be injected below the skin with very thin needles (29-30 G, equivalent to a diameter of 0.33 and 0.30 mm, respectively). This condition entails the use of easily extrudable, low viscosity hydrogels, formed by derivatized HA in bidistilled water, in a buffer saline solution, in a sterile physiological solution or in water for injectable preparations. These usage conditions are tightly linked to the possibility of tuning the viscosity of this hydrogel, while remaining in the described parameters of derivatization degree and concentration expressed in w/v %.

Finally, the hydrogel of the invention can be used in general surgery, e.g., in gynecology. Often, the adverse events encountered in gynecologic surgery refer to problems related to fertility, to chronic pelvic inflammations or to endometriosis. In this case too, the product in form of hydrogel can be associated to an anti-inflammatory drug in order to reduce at a minimum the risk of inflammation during surgical intervention, such as diclofenac, commonly adopted in this kind of surgery and capable to considerably reduce painful symptomatology.

As general indications, in the case of cosmetic surgery it turns out to be suitable a hydrogel of the invention having a viscosity comprised between 5 and 20 Pa·s; in maxillo-facial surgery it is possible to use a hydrogel with a viscosity comprised between 50 and 100 Pa·s; in abdominal surgery it is possible to use a hydrogel with viscosity comprised between 150 and 450 Pa·s; finally, in general (in particular gynecologic) surgery it is possible to use a hydrogel with viscosity comprised between 60 and 140 Pa·s.

Preferably, these hydrogels are obtained with a 3% w/v concentration in water of a HA with a derivatization degree of 2.7% for use in cosmetic surgery; with a 6% w/v concentration in water of a HA with a derivatization degree of 3.5% for use in maxillo-facial surgery; with a 10% w/v concentration in water of a HA with a derivatization degree of 7% for use in abdominal surgery; and with a 8% w/v concentration in water of a HA with a derivatization degree of 3.5% for use in general, and particularly gynecological, surgery.

In a preferred embodiment, the hydrogels obtained from HA derivatives described above are loaded with at least one of the following bioactive compounds:
compounds capable of affecting the stability of the biofilm protecting bacteria, chosen among cysteine and its derivatives and D-amino acids;
NSAIDs;
anesthetics for local use;
opioids and tramadol; and
growth factors.

A hydrogel loaded with one or more bioactive compounds will be referred to in the rest of the description as a "bioactive hydrogel", in order to distinguish it from a hydrogel obtained solely from the HA derivative and bidistilled water, a buffer saline solution, a sterile physiological solution or water for injectable preparations (the object of the first embodiment of the invention), that will be referred to simply as "hydrogel".

The inventors have observed that the bioactive hydrogels according to this second embodiment of the invention, further to having chemical properties that make them capable of remaining stable in the site of injection or implant for at least the first days after operation (and in case of implants, their rheological properties are such that they remain adhered onto the implant surface), also have properties of release of the bioactive compounds that make them suitable for carrying out the pharmacological or biological actions they are intended for.

A first possible action that can be exerted by a bioactive hydrogel of the invention is an antibacterial action. It is known that bacteria colonies, once established in a site, produce a biofilm consisting of macromolecules including proteins and polysaccharides which protects the bacterial colony and renders general antibiotic and biocide treatments ineffective.

Cysteine and its derivatives and D-amino acids have the capability to interfere with the biofilm protecting colonies of bacteria; these compounds are referred to below also as "anti-biofilm compounds". A bioactive hydrogel of the invention, loaded with cysteine or a cysteine derivative, or with a D-amino acid, avoid the formation of the biofilm, or weaken it, so as to leave the bacteria exposed to the action of the immune system of the patient that has undergone the orthopedic operation, or of other antibacterial agents (e.g., antibiotics) that can be administered orally, parenterally, or locally; local administration is preferably obtained by loading the antibacterial agent in the bioactive hydrogel itself, admixed with the cited anti-biofilm compounds.

Examples of suitable cysteine-related compounds are L-cysteine, D-cysteine, D-L cysteine, D-L homocystein, L-cysteine methyl ester, L-cysteine ethyl ester, N-carbamoyl cysteine, cysteamine, N-(2-mercaptoisobutyryl)-L-cysteine, N-(2-mercaptopropionyl)-L-cysteine A, N-(2-mercaptopropionyl)-L-cysteine B, N-(32-mercaptopropionyl)-L-cysteine, L-cysteine ethyl ester hydrochloride, L-cysteine methyl ester hydrochloride, nacysteline (a lysine salt of N-acetylcysteine), N-acetylcysteine and derivatives thereof. Among these, preferred is N-acetylcysteine, the properties of which are described, e.g., in the paper "Influence of N-acetylcysteine on the formation of biofilm by *Staphylococcus epidermidis*", C. Pérez-Giraldo et al., Journal of Antimicrobial Chemotherapy (1997) 39, 643-646, and are exploited for instance in patent U.S. Pat. No. 6,475,434 B1 for the coating of medical devices.

Examples of suitable D-amino acids are D-tyrosine, D-leucine, D-tryptophan and D-methionine. The properties of D-amino acids in the disruption of the biofilm are described for instance in the paper "D-Amino acids trigger biofilm disassembly", I. Kolodkin-Gal et al., Science, vol. 328, no. 5978, May 2010, 627-629.

Another important function that can be fulfilled by the bioactive hydrogels of the invention is postoperative pain control.

This result can be achieved by loading the hydrogel with one or more compounds used to this end, and in particular NSAIDs, anesthetics for local use and opioid analgesics. Useful NSAIDs are, for instance (but not limited to), acetaminophen, acetylsalicylic acid, benorilate, bromelain, carprofen, celecoxib, cinnoxicam, clamidoxic acid, clonixin, diclofenac, diflumidone, diflunisal, etoricoxib, fenclofenac, fendosal, fenoprofen, flufenamic acid, fluquazone, flurbiprofen, ibufenac, ibuprofen, iguratimod, indometacin, indoprofen, isofezolac, ketoprofen, ketorolac, licofelone, lornoxicam, lumiracoxib, meclofenamic acid, mefenamic acid, meloxicam, metamizole, naproxen, niflumic acid, nimesulide, orpanoxin, oxatiaprim, parecoxib, piroxicam, robenacoxib, rofecoxib, seaprose-S, serratiopeptidase, sudoxicam, sulfanizolon, sulindac, suprofen, tenoxicam, tiflamizole, tomoxiprole and valdecoxib.

Useful anaesthetics for local use are, among others, bupivacaine, chloroprocaine, levobupivacaine, lidocaine, prilocaine, procaine ropivacaine and carbocaine.

Useful opioid analgesics are, among others, buprenorphine, butorphanol, dextromethorphan, fentanyl, etorphine, idromorphone, loperamid, morphine, oxycodone, pethidine, sufetanil and tramadol.

Finally, a further very important class of functional compounds that can be loaded into the bioactive hydrogels of the invention is represented by growth factors. These are generally glycoproteins that have the function of stimulating basic mechanisms involved in the regeneration of tissues. A non-exhaustive list of growth factors that can be carried to and released into the operation site through the bioactive hydrogels of the invention comprises bone morphogenetic protein 2 (BMP2) and bone morphogenetic protein (BMP7), fibroblast growth factors (FGFs), insulin-like growth factors (IGFs), epidermal growth factors (EGFs), vascular endothelial growth factor (VEGFs), transforming growth factor beta (TGF-β), and platelet-derived growth factors (PDGFs).

The bioactive hydrogel of the invention can be loaded with more than one of the bioactive compounds listed above, even belonging to different categories: for instance, can be present at the same time at least an anti-biofilm compound, at least a pain control compound and at least a growth factor.

The bioactive hydrogel has a concentration relative to the HA derivative comprised between 1 and 35% w/v, preferably between 2 and 10% w/v, and a concentration relative to the bioactive compounds comprised between 0.001% and 80% w/v, preferably between 1 and 10% w/v, depending on the specific bioactive compound(s), and the intended use; in case more bioactive compounds (even belonging to classes with different pharmacological or biological functions) are loaded into the hydrogel, the above given concentration is referred to the sum of these compounds.

To obtain these final concentrations, a convenient method is to produce separately the hydrogel with no bioactive compound(s), and mix it with one or more solutions of the latter. The starting components of the bioactive hydrogel may have concentrations in wide ranges and be mixed in different ratios, as it will be apparent to the skilled technician. In more common cases, the volume of the hydrogel used is greater than the volume of solution of bioactive compound(s); for this reason, the concentration of the starting hydrogel will have a HA derivative concentration close to the concentration of the same derivative in the bioactive hydrogel, comprised between 1 and 35% w/v and preferably 2-10% w/v. To the contrary, the concentration of the starting bioactive compound(s) solution may greatly differ from the concentration of said compound (s) in the bioactive hydrogel, and these compounds may even be loaded into the hydrogel in pure form (namely, concentration of 100%).

Conveniently, in preparing the bioactive hydrogel, the HA derivative and the bioactive compound(s) solution are mixed in a volume ratio comprised between 20:1 and 1:1, preferably between 10:1 and 1.5:1. To avoid that parts of the bioactive hydrogel are not sufficiently loaded with the drug, the mixture formed by the two components is preferably homogenized by stirring or mixing, that can simply be done manually or with automatic means.

The bioactive hydrogel of the invention can thus be provided in the form of kit-of-parts. The kit makes it possible for the surgeon to decide the actual loading of bioactive compound(s) in the bioactive hydrogel, both as to the nature of said compound(s) and to its (their) concentration, just before or even during the surgical intervention, allowing the best tailoring of the bioactive injection material or coating onto the prosthesis, in view of the specific needs of the patients (e.g., known intolerances to specific bioactive compounds) or of the specific intervention. The kit comprises a first composition that is the hydrogel prepared with the sole HA derivative and water (added as bidistilled water, buffer solution or physiological solution) and one or more compositions comprising the bioactive compound(s); in case of use of more than one bioactive compounds, these may be added in form of one single solution or more solutions (e.g., one solution per bioactive compound).

In case of use of a kit, the bioactive hydrogel is produced just before its use, by mixing in the desired ratio the hydrogel of the HA derivative with the chosen bioactive compound; and, in a short term after its preparation, injected in the area of bone fracture or cavity or applied to the surface of a prosthesis to be implanted. The injection into bone damaged parts may be realized by a needle and a syringe, under ecographic guide. The application of the bioactive hydrogel onto the prosthesis may be realized by various methods, such as immersion of the prosthesis into the bioactive hydrogel, spraying, spreading, brushing and the like.

The bioactive hydrogels of the invention have a rate of reabsorption in the body such that the release of the bioactive compounds always lasts at least 6 hours after the orthopedic intervention, that are the most critical from the point of view of bacterial attack, and often such release takes place continuously over the first 48-72 hours after surgery, so as to cover the critical periods after intervention at least with respect to the control of bacterial infections and postoperative pain.

The invention will be further illustrated by means of the following examples, intended to assist in understanding the invention and not to be construed as specifically limiting the invention described and claimed herein.

In the examples, the following materials and equipments have been used:

Materials:

The sodium salt of hyaluronic acid (MW 1500 kDa) has been provided by Gelphifarma (Lodi, Italy), the prosthesis used is model Recta of Adler Ortho s.r.l. (Bologna, Italy); D,L-polylactic acid (PLA) (MW 8 kDa) is sold by Bidachem-Boeringher Ingelheim (Milan, Italy), with the name RESOMER R 202; N,N'-Dicyclohexylcarbodiimide (DCC), N-hydroxysuccinimide (NHS), 1,1'carbonyldiimidazole (CDI), tetrabutylammonium hydroxide (TBA-OH), hydrochloric acid, the Dulbecco's phosphate buffered saline (DPBS pH 7.4), the reagent in o-phthaldialdehyde (OPA) solution and N-acetylcysteine were purchased from Sigma Aldrich (Milan, Italy). The Dowex 50Wx8-200 cation exchange resin, diethylamine (DEA), anhydrous dimethyl sulfoxide (DMSO) and O-2-aminoethyl-O'-methylpolyethylene glycol 5000 (PEG-$NH_2$) were obtained from Fluka (Milan, Italy).

Equipments:

The $^1$H-NMR spectra were obtained with a Brucker AC-300 instrument. The FT-IR spectra were recorded as KBr discs in the range 4000-400 $cm^{-1}$ using a Perkin Elmer spectrophotometer 1720 and Fourier transformed, with a 1 $cm^{-1}$ resolution; each spectrum was recorded after 100 scans. SEC analysis was carried out using a SEC multidetector system equipped with a Water 600 pump, a Water 410 refractive index meter, and a linear column provided by Water (particle size 5 μm). The calibration curve was determined using hyaluronic acid standards purchased from Hyalose (USA). The elution conditions were the following: phosphate buffer 200 mM (pH 6.5)/MeOH 90:10 (v/v), flow rate 0.6 ml/min, at a temperature of 35° C.

Example 1

This example is about the formation of the tetrabutylammonium salt of HA (HA-TBA). 1 g of HA of molecular weight 1500 kDa is dissolved in 100 ml of a HCl solution having pH 0.5, and left to react at 37° C. for 24 hours. The resulting product has an average MW of 230 kDa, as determined by SEC analysis. To this product, tetrabutylammonium hydroxide (TBA-OH) is added until pH 7 is reached; the reaction mixture is then subjected to exhaustive dialysis.

The resulting HA-TBA salt is recovered by freeze drying and characterized by $^1$H-NMR ($D_2O$) analysis which confirms that exchange with TBA has taken place with a yield of 100%. The $^1$H-NMR ($D_2O$) spectrum of the HA-TBA shows signals at: δ 0.97 (m, 12H, $N^+$—($CH_2$—$CH_2$—$CH_2$—$CH_3$)$_4$); δ 1.40 (m, 8H, $N^+$—($CH_2$—$CH_2$—$CH_2$—$CH_3$)$_4$); δ 1.64 (m, 8H, $N^+$—($CH_2$—$CH_2$—$CH_2$—$CH_3$)$_4$); δ 2.04 (s, 3H, —NH—CO—$CH_3$); δ 3.82 (m, 8H, $N^+$($CH_2$—$CH_2$—$CH_2$—$CH_3$)$_4$).

Example 2

This example is about the activation of a polyester (PLA) with NHS.

The synthesis is carried out following the synthesis route of polylactic-co-glycolic acid (PLGA) derivative described in the paper "Folate receptor targeted biodegradable polymeric doxorubicin micelles", Yoo H. S. et al, Journal of Controlled Release, (2004) 96: 273-283.

2.4 g of PLA of average MW 8 kDa are dissolved in 30 ml of dichloromethane. To this solution are first added 0.25 g of the condensing agent dicyclohexylcarbodiimide (DCC), and then 0.14 g of NHS, allowing the reaction to take place at ambient temperature for 24 hours. After this period, the reaction mixture is concentrated by partial evaporation of dichloromethane and the product is precipitated in ethanol and repeatedly washed in the same solvent. The solid obtained is then filtered off and dried under vacuum. A white crystalline solid is obtained, with a yield exceeding 80% by weight on the starting PLA quantity. The $^1$H-NMR spectrum confirms that activation of the PLA carboxyl group with N-hydroxysuccinimide has taken place. The yield of derivatization, expressed as the ratio of bound moles of NHS to moles of a single PLA chain, is 90%.

The $^1$H-NMR spectrum of the product PLA-NHS ($CDCl_3$) shows signals at: δ 1.5 and δ 1.6 (d, 3H, —O—CO—CH($CH_3$)—OH; δ, 3H, O—CO—CH($CH_3$)—O—), δ 2.80 (m, 4H, —OC—$CH_2$—$CH_2$—CO—); δ 4.3 and δ 5.2 (m, 1H, —O—CO—CH($CH_3$)—OH; m, 1H, —O—CO—CH ($CH_3$)—O—).

Example 3

This example is about the synthesis of a HA-PLA derivative.

HA-TBA prepared as described in Example 1 and PLA-NHS prepared as described in Example 2 are reacted in three different ratios, to obtain products of different PLA-derivatization degree. Three HA-TBA solutions of same concentration are obtained by dissolving for each solution 600 mg of HA-TBA in 48 ml of anhydrous DMSO in the presence of 576 μl of the catalyst diethylamine (DEA). Apart, three solutions of different concentration of PLA-NHS are prepared by dissolving, respectively, 1.5, 3.6 and 7.2 g of PLA-NHS in 6 ml of anhydrous DMSO. The three PLA-NHS solutions are added dropwise over a one hour period to the HA-TBA solutions; the nominal ratio of moles of PLA-NHS to moles of N-acetyl-D-glucosamine units of HA in the three reacting mixtures is 0.2, 0.5 and 1.0, respectively. The three different derivatives are named in the following HA-$PLA_{(A)}$, HA-$PLA_{(B)}$ and HA-$PLA_{(C)}$.

After 24 hours under an anhydrous argon atmosphere 40° C., each reaction mixture is passed through a Dowex sodium exchange resin to exchange the TBA with $Na^+$. The eluate is then placed under dialysis against distilled water to eliminate DMSO, then frozen and dried by freeze-drying. The solid is washed repeatedly in acetone and dried again.

The FT-IR spectrum of the obtained HA-PLA derivatives shows a band at 3540 cm$^{-1}$ ($v_{as}$ OH+$v_{as}$ NH of HA), bands at 1757 cm$^{-1}$ ($v_{as}$ COO of PLA), 1623 cm$^{-1}$ (amide I of HA), 1456 cm$^{-1}$ ($v_{as}$, CH$_3$ of PLA), 1382 cm$^{-1}$ ($v_s$ CH$_3$ of PLA), 1189 cm$^{-1}$ ($v_s$ C—O—C of the ester groups of PLA), 1089 cm$^{-1}$ and 1048 cm$^{-1}$ (v C—O alcoholic and etheric of HA).

The $^1$H-NMR spectrum of the obtained HA$_{LMW}$-PLA derivatives (DMSO-d$_6$/D$_2$O 90:10) shows: δ 1.25 and δ 1.45 (2d, —O—CO—CH(CH$_3$)—O— of PLA); δ 1.85 (s, 3H, —NH—CO—CH$_3$ of HA) δ 5.1 ppm (m, —O—CO—CH(CH$_3$)— of PLA).

The derivatization degree (DD, %) in PLA of the HA-PLA derivatives is calculated by evaluating the number of PLA chains from the integrals of the two peaks relative to the protons at δ 1.25 and δ 1.45 (attributable to the methyl groups of the PLA chain) and the number of N-acetyl-D-glucosamine present in the HA from the integral relative to the protons at δ 1.85 attributable to the —NHCOCH$_3$ group, and then applying the formula:

DD=(No. moles PLA/No. moles glucosamine units)×100,

The results of derivatization degree for the three different reaction mixtures are as given in Table 1:

TABLE 1

| Sample | DD (%) in PLA |
|---|---|
| HA-PLA$_{(A)}$ | 2.7 |
| HA-PLA$_{(B)}$ | 3.5 |
| HA-PLA$_{(c)}$ | 7 |

Example 4

This example is about the synthesis of a PEG-HA-PLA derivative.

The preparation of HA-PLA derivatives described in Example 3 is repeated, with the differences that in this case are used three solutions obtained by dissolving in 6 ml of anhydrous DMSO, respectively, 5.2, 7.2 and 14.0 g of PLA-NHS (corresponding to nominal ratios of moles of PLA-NHS to moles of N-acetyl-D-glucosamine units of HA of 0.7, 1.0 and 2.0, respectively), and that no exchange of TBA ions is carried out at the end of the reaction. The solid product obtained is recovered by filtration and washed repeatedly in acetone and the product is dried under vacuum.

300 mg of each HA-PLA product prepared by using 5.2, 7.2 and 14.0 g of PLA-NHS are dissolved in 24 ml of anhydrous DMSO under argon, obtaining three solutions. Apart are prepared three solutions of different concentration of PEG-NH$_2$, obtained by dissolving in 6 ml of anhydrous DMSO, respectively, 0.42, 0.43 and 0.84 g of PEG-NH$_2$ of average molecular weight 5000 Da. to each of the three solutions is added dropwise a solution. The three PEG-NH$_2$ solutions are added dropwise to the HA-PLA solutions, with the proviso that PEG-NH$_2$ solutions of higher concentration are added to solutions of HA-PLA products obtained with higher amount of PLA-NHS. The reaction is carried out in the presence of DCC and NHS activators added in quantities equimolar to the PEG-NH$_2$ used. After 24 hours at ambient temperature, the reaction mixture is brought to 5° C. for 10 min to facilitate precipitation of the dicyclohexylurea (DCU) formed, which is then removed from the reaction mixture by filtration. Subsequently, the filtered reaction mixture is eluted in Dowex 50 W×8-200 sodium resin to remove the TBA and the eluate is dialyzed against water using a Spectra/por Tubing dialysis membrane with cut-off of 3.5 kDa, to completely remove DMSO. The product recovered after freeze-drying is dissolved in water and eluted in Dowex 50 W×8-200 acid resin; the eluate is finally purified by dialysis against concentrated NaCl solutions (5% w/v) for three days and against bidistilled water for the last two days, using a Spectra/por Tubing 12000/14000 Da dialysis membrane. The solution is finally dried by freeze-drying, and the obtained PEG-HA-PLA derivative shows the following data at $^1$H-NMR analysis [THF-d$_8$/D$_2$O 1/1]: δ 1.4 and 1.6 [2d, 3H, —O—CO—CH(CH$_3$)—O— of PLA], δ 2.1 (s, 3H, —NH—CO—CH$_3$ of HA), δ 4.0 (m, 4H, —CH$_2$—CH$_2$— of PEG), δ 5.40 [m, 1H, —O—COCH(CH$_3$)— of PLA].

The three different derivatives obtained are named in the following PEG-HA-PLA$_{(D)}$, PEG-HA-PLA$_{(E)}$ and PEG-HA-PLA$_{(F)}$. The derivatization degree (DD, %) in PEG of the PEG-HA-PLA derivatives is obtained comparing the integrals of the two peaks relative to the protons attributable to the —CH$_2$—CH$_2$— portion of the PEG-NH$_2$ (δ 4.0), with the integral relative to the protons (δ 2.1) attributable to the —NHCOCH$_3$ group pertaining to the HA N-acetylglucosamine residues, and then applying the formula:

DD=(No. moles PEG/No. moles glucosamine units)×100.

The results of derivatization degree for the three different reaction mixtures are as given in Table 2:

TABLE 2

| Sample | DD (%) in PLA | DD (%) in PEG |
|---|---|---|
| PEG-HA-PLA$_{(D)}$ | 5 | 9 |
| PEG-HA-PLA$_{(E)}$ | 7.2 | 9 |
| PEG-HA-PLA$_{(F)}$ | 13.9 | 17.9 |

Example 5

This example is about the implantation of a titanium prosthesis coated with a hydrogel of the invention.

A lyophilized human femur from a bone bank is obtained and its head is removed, as commonly known in total hip replacement surgery. A seat for the prosthesis is prepared in the femur shaft in a way that is very well known to the experts in the surgery applications. A seat for the prosthesis is obtained in the bone diaphysis in a way that is very well known to the ones skilled in this art. The femur shaft is open longitudinally by cutting it along a plane essentially parallel to its axis, for a length slightly greater than the prosthesis length, and then by cutting perpendicularly to said axis, so as to remove one of the two long "prongs" produced by the first cut. This way, the medullary canal is exposed in the parts in which the prosthesis will be then accommodated, both in the part that remains connected to the main body of the femur, and in the detached "prong". Then these are rejoined and firmly kept together by means of metal and plastic fasteners. Apart, the prosthesis is prepared. The prosthesis used is model Recta of Adler Ortho s.r.l. of Bologna, Italy. Before insertion in the seat obtained in the femur, the exterior surface of the prosthesis (apart from the upper part, to be connected with a modular neck of the same company in actual surgery) is coated by manual brushing with a hydrogel prepared with a HA derivative produced as described in Example 3. The preparation of the bioactive hydrogel is briefly as follows: to 3 ml of hydrogel, prepared at 10% w/v HA-PLA (DD=7%) in water for injectables, 2 ml of a 10% w/v solution of N-acetylcysteine in injectable water are added and thoroughly mixed for 60 seconds, to obtain a uniform hydrogel having 6% HA charge, and 4% N-acetylcysteine charge. The hydrogel is charged with 0.5% of methylene blue, in order to make the presence and distribution of the hydrogeol more visible in subsequent inspections both on the prosthesis and in the seat in the femur. The prosthesis is then inserted by press-fit into the seat previously obtained in the femur. After 3 minutes, the fasteners are removed, the femur is opened and the distribution of the hydrogel in the inner surfaces of the medullary bone cavity and onto the surface of the prosthesis is visually inspected.

As results from visual inspection, at the end of the procedure the hydrogel is tightly adherent onto the prosthesis surface, as well as evenly distributed inside the prosthesis seat in the bone. This result confirms that the hydrogel of the invention has rheological properties suitable for use as coatings of implants, in that it is not removed from the prosthesis surface despite the strong shear force the prosthesis experiences during insertion in its implant seat. This affords the presence of a source of agents in the site of the implant for a period sufficient to avoid the establishing of a bacterial colony.

Example 6

This example is about the use in cosmetic surgery of a hydrogel of the invention.

A product is prepared following the procedure of Example 3, with particular reference to the derivative named HA-PLA$_{(A)}$. 0.150 g of the derivative HA-PLA$_{(A)}$ are hydrated with 5 ml of sterile physiological solution, obtaining a hydrogel of concentration 3% w/v. Upon completion of hydration, the hydrated product is distributed into five 1 ml glass syringes provided with Luer-lock fitting, in order to allow the insertion of a 29 or 30 G needle before use. The syringes filled with the hydrated product are sterilized with steam. The thus obtained product may be used as bio-revitalizing or reabsorbable filler.

Example 7

This example is about the use in maxillo-facial surgery of a hydrogel of the invention. A hydrogel is prepared following the procedure of Example 3, with particular reference to the derivative named HA-PLA$_{(B)}$. 0.300 g of the derivative HA-PLA$_{(B)}$ are hydrated with 5 ml of water for injectable preparations, obtaining a hydrogel of concentration 6% w/v. The hydrated product is distributed into five 1 ml glass syringes provided with Luer-lock fitting, in order to allow the insertion of a cannula before use. The syringes filled with the hydrated product are sterilized with steam.

Example 8

This example is about the use in abdominal surgery of a hydrogel of the invention.

As stated above, a hydrogel for use in this kind of surgery must have high viscosity in order to efficiently carry out an anti-adhesion action.

A hydrogel is prepared following the procedure of Example 3, with particular reference to the derivative named HA-PLA$_{(C)}$. 0.500 g of the derivative HA-PLA$_{(C)}$ are hydrated with 5 ml of water for injectable preparations, obtaining a hydrogel of concentration 10% w/v. The hydrated product is distributed into five 1 ml glass syringes provided with Luer-lock fitting, in order to allow the insertion of a cannula before use. The syringes filled with the hydrated product are sterilized with steam.

Example 9

This example is about the use in general surgery of a hydrogel of the invention.

A hydrogel is prepared following the procedure of Example 3, with particular reference to the derivative named HA-PLA$_{(B)}$. 0.400 g of the derivative HA-PLA$_{(B)}$ are hydrated with 5 ml of sterile physiological solution, obtaining a hydrogel of concentration 8% w/v. The hydrated product is distributed into five 1 ml glass syringes provided with Luer-lock fitting, in order to allow the insertion of a cannula before use. The syringes filled with the hydrated product are sterilized with steam.

The invention claimed is:

1. A hydrogel comprising water and a hyaluronic acid derivative, wherein:
    the hyaluronic acid derivative comprises hyaluronic acid (HA), or a salt thereof, of molecular weight comprised between 50,000 and 3,500,000 Da, onto the N-acetyl-D-glucosamine moieties of which are grafted chains of a biodegradable and biocompatible polyester of molecular weight comprised between 3,000 and 900,000 Da, in an amount such that the derivative comprises between 1 and 50 of said polyester chains per 100 repeating units of D-glucuronic acid/N-acetyl-D-glucosamine of hyaluronic acid;
    the concentration of said hyaluronic acid derivative in the hydrogel is between 2 and 10% w/v, and
    the hydrogel has a shelf life of at least 6 month at ambient temperature.

2. The hydrogel according to claim 1, wherein said polyester is selected from the group consisting of poly-lactic acid of molecular weight in the range between 3,000 and 150,000 Da, poly-glycolic acid of molecular weight in the range between 1,000 and 900,000 Da, poly-caprolactone of molecular weight in the range between 3,000 and 900,000 Da, mixtures and copolymers thereof.

3. The hydrogel according to claim 1, wherein onto D-glucuronic acid units of said hyaluronic acid or salt thereof are further grafted chains of polyethylene glycol.

4. The hydrogel according to claim 3, wherein said polyethylene glycol has molecular weight in the range between 400 Da and 20,000 Da.

5. The hydrogel according to claim 3, wherein the number of D-glucuronic acid units to which are grafted said chains of polyethylene glycol is between 5 and 20% of the total number of such units present in the HA chain.

6. A bioactive hydrogel comprising a hydrogel according to claim 1 and at least one of the following bioactive compounds:
    compounds capable of affecting the stability of the biofilm protecting bacteria, chosen among cysteine and its derivatives and D-amino acids;
    NSAIDs;
    anesthetics for local use;
    opioids and tramadol; and
    growth factors.

7. A method for the use of the bioactive hydrogel of claim 6, characterized in that said bioactive hydrogel is produced by mixing in the desired ratio a hydrogel of claim 1 with the chosen bioactive compound or compounds, and said mixing takes place in a short term before the injection of the bioactive hydrogel in the area of a bone fracture or cavity or before the application of the bioactive hydrogel to the surface of a prosthesis to be implanted.

8. A kit for use in the method of claim 7, comprising at least two compositions, the first one being a hydrogel formed by the HA derivative and water having a concentration of HA derivative comprised between 2 and 10% w/v, the second one or further ones being one or more compositions comprising one or more bioactive compounds.

9. A prosthesis for implant in the human or animal body coated with a hydrogel according to claim 1.

10. A prosthesis for implant in the human or animal body coated with a bioactive hydrogel according to claim 6.

11. The kit of claim 8 for use in cosmetic surgery, in which said hydrogel has a viscosity comprised between 5 and 20 Pa·s.

12. The kit of claim 8 for use in maxillo-facial surgery, in which said hydrogel has a viscosity comprised between 50 and 100 Pa·s.

13. The kit of claim 8 for use in abdominal surgery, in which said hydrogel has a viscosity comprised between 150 and 450 Pa·s.

14. The kit of claim 8 for use in general and gynecologic surgery, in which said hydrogel has a viscosity comprised between 60 and 140 Pa·s.

15. A prosthesis for implant in the human or animal body coated with a hydrogel according to claim 3.

16. A prosthesis for implant in the human or animal body coated with a hydrogel according to claim 5.

* * * * *